United States Patent
Enomoto et al.

(10) Patent No.: US 9,068,024 B2
(45) Date of Patent: Jun. 30, 2015

(54) 2,2-DIMETHOXY-1,2-DI[4-(METH)ACRYLOYLOXY]PHENYLETHANE-1-ONE, METHOD FOR PRODUCING THE SAME, RADICAL POLYMERIZATION INITIATOR AND PHOTOCURABLE COMPOSITION

(75) Inventors: Satoshi Enomoto, Chiba (JP); Yuki Hara, Chiba (JP)

(73) Assignee: TOYO GOSEI CO., LTD., Chiba (JP)

( * ) Notice: Subject to any disclaimer, the term of this patent is extended or adjusted under 35 U.S.C. 154(b) by 187 days.

(21) Appl. No.: 13/983,106

(22) PCT Filed: Jan. 30, 2012

(86) PCT No.: PCT/JP2012/051943
§ 371 (c)(1),
(2), (4) Date: Aug. 1, 2013

(87) PCT Pub. No.: WO2012/105479
PCT Pub. Date: Aug. 9, 2012

(65) Prior Publication Data
US 2013/0324633 A1 Dec. 5, 2013

(30) Foreign Application Priority Data
Feb. 2, 2011 (JP) ................. 2011-021231

(51) Int. Cl.
*C07C 69/54* (2006.01)
*C08F 2/50* (2006.01)

(52) U.S. Cl.
CPC .. *C08F 2/50* (2013.01); *C07C 69/54* (2013.01)

(58) Field of Classification Search
CPC ........... C07C 69/52; C07C 69/54; C08F 2/50; G03F 7/025
See application file for complete search history.

(56) References Cited

U.S. PATENT DOCUMENTS

| | | | |
|---|---|---|---|
| 4,190,602 A | 2/1980 | Brunisholz et al. | |
| 6,048,667 A | 4/2000 | Eldin et al. | |
| 2005/0119433 A1* | 6/2005 | Sakayori | 526/348 |
| 2005/0264737 A1* | 12/2005 | Kataoka et al. | 349/124 |
| 2006/0103804 A1* | 5/2006 | Hirosawa | 349/183 |
| 2010/0272925 A1* | 10/2010 | Goetz et al. | 428/1.1 |
| 2011/0095229 A1* | 4/2011 | Lee et al. | 252/299.61 |
| 2011/0102720 A1* | 5/2011 | Mizusaki et al. | 349/123 |
| 2013/0169916 A1* | 7/2013 | Mizusaki et al. | 349/123 |
| 2014/0139794 A1* | 5/2014 | Ohnishi et al. | 349/123 |
| 2014/0168586 A1* | 6/2014 | Mizusaki et al. | 349/123 |
| 2014/0333879 A1* | 11/2014 | Noma et al. | 349/124 |

FOREIGN PATENT DOCUMENTS

| | | |
|---|---|---|
| JP | 49-55646 | 5/1974 |
| JP | 02-180909 | 7/1990 |
| JP | 04-305574 | 10/1992 |
| JP | 05-310635 | 11/1993 |
| JP | 11-509329 | 8/1999 |
| JP | 2005-082679 | 3/2005 |
| JP | 2009-138150 | 6/2009 |
| WO | WO2012032857 A1 * | 3/2012 |

OTHER PUBLICATIONS

Enomoto et al. Surface Patterned Graft Copolymerization of Hydrophilic Monomers onto Hydrophobic Polymer Film Upon UV Irradiation. Journal of Polymer Science, Part A: Polymer Chemistry. 2014, 52, 2288-2829.*

Francesco Babudri et al., "A Direct Access to α-Diones from Oxalyl Chloride", Tetrahedron Letters vol. 36, No. 40, pp. 7305-7308, (1995).

International Search Report PCT/JP2012/051943 dated Mar. 6, 2012, with English translation.

* cited by examiner

*Primary Examiner* — Sanza McClendon
(74) *Attorney, Agent, or Firm* — Young & Thompson

(57) ABSTRACT

The invention provides 2,2-dimethoxy-1,2-di-[4-(meth)acryloyloxy]phenylethane-1-one represented by the following formula (A):

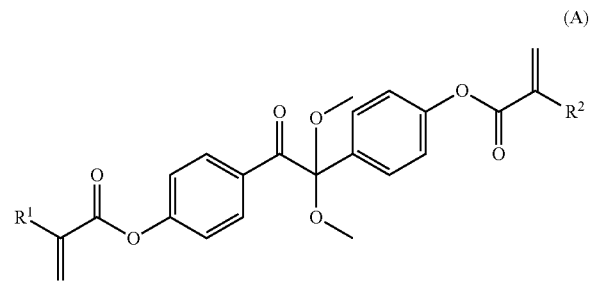

(A)

(wherein $R^1$ and $R^2$, which may be identical to or different from each other, each represent a hydrogen atom or a methyl group).

5 Claims, No Drawings

2,2-DIMETHOXY-1,2-DI[4-(METH)ACRYLOYLOXY]PHENYLETHANE-1-ONE, METHOD FOR PRODUCING THE SAME, RADICAL POLYMERIZATION INITIATOR AND PHOTOCURABLE COMPOSITION

TECHNICAL FIELD

The present invention relates to a novel compound serving as a radical polymerization initiator, which generates radicals through irradiation with light such as a UV ray, to a production method therefor, to a radical polymerization initiator, and to a photocurable composition.

BACKGROUND ART

In UV-curable ink for lithography, flexography, and silk screening, solder resist, etching resist for production of industrial electronic material or the like, color filter resist, UV powder coating, aqueous UV coating, coating with UV-absorber, wood article finish coating, plastics, metal coating, etc., there has been employed a photocurable composition containing a radical-polymerizable compound (i.e., a radical-polymerizable monomer) and a radical polymerization initiator, which generates radicals through irradiation with light such as a UV ray for initiating polymerization of the radical-polymerizable compound. A typical radical polymerization initiator is an acetophenone-type radical polymerization initiator (see Patent Documents 1 and 2).

One known acetophenone-type radical polymerization initiator is 2,2-dimethoxy-1,2-diphenylethan-1-one. The compound can generate radicals via self-cleavage through irradiation with light such as a UV ray, to thereby initiate polymerization of a radical-polymerizable compound, and is commercially available as IRGACURE 651 (product of BASF). As compared with other acetophenone-type radical polymerization initiators; e.g., 1-hydroxycyclohexyl phenyl ketone (IRGACURE 184, product of BASF) and 2-hydroxy-1-{4-[4-{2-hydroxy-2-methylpropionyl}-benzyl]-phenyl}-2-methylpropan-1-one (IRGACURE 127, product of BASF), 2,2-dimethoxy-1,2-diphenylethan-1-one has higher absorbance to 365 nm light. This property is advantageous, for the compound can effectively utilize i-line (wavelength: 365 nm), which is a predominant component of high-pressure mercury lamps and other industrially useful light sources.

Differing from thermal polymerization, photopolymerization by use of such a radical polymerization initiator can provide a cured product through irradiation with light such as a UV ray at room temperature or thereabout without heating. Through photopolymerization, the risk of material deterioration is reduced, and a cured product can be obtained in a considerably shorter period of time as compared with thermal polymerization. Thus, photopolymerization is a useful technique widely employed in the industry. However, photopolymerization has a drawback in that a component originating from a radical polymerization initiator remaining in the cured product bleeds out with lapse of time. The bleeding out increases considerably when the amount of radical polymerization initiator is increased for shortening curing time.

Compounds such as 1-[4-(2-hydroxyethoxy)-phenyl]-2-hydroxy-2-methyl-1-propan-1-one (IRGACURE 2959, product of BASF) and 2-hydroxy-1-{4-[4-{2-hydroxy-2-methylpropionyl}-benzyl]-phenyl}-2-methylpropan-1-one (IRGACURE 127, product of BASF) are low-volatile compounds, and give off less odor after curing. These compounds are resistant to bleeding out, but the resistance is not satisfactory.

Hitherto, a technique of reducing bleeding out has been disclosed (see Patent Documents 3 and 4). The technique employs species of (meth)acryloyloxy group-incorporated 2,2-dimethoxy-1,2-diphenylethan-1-one.

However, the compounds disclosed in Patent Documents 3 and 4 have low crystallinity and assume the form of oil. Therefore, in production of these compounds, crude products must be purified through distillation, column chromatography, or a like technique, making the production steps cumbersome. Particularly, since the ketal structure and the (meth)acryloyloxy groups of 2,2-dimethoxy-1,2-diphenylethan-1-one have poor thermal stability, these moieties may undergo thermal decomposition or thermal polymerization during large-scale purification by distillation at high temperature. Also, performing column chromatography disadvantageously elevates production cost.

PRIOR ART DOCUMENTS

Patent Documents

Patent Document 1: Japanese Patent Application Laid-Open (kokai) No. Hei 02-180909
Patent Document 2: Japanese Patent Application Laid-Open (kokai) No. Sho 49-55646
Patent Document 3: Japanese Patent Application Laid-Open (kokai) No. Hei 04-305574
Patent Document 4: Japanese Patent Application Laid-Open (kokai) No. Hei 05-310635

Non-Patent Documents

Non-Patent Document 1: Tetrahedron Letters, Vol. 36., (40) (1995), p. 7305-7308

SUMMARY OF THE INVENTION

Problems to be Solved by the Invention

In view of the forgoing, an object of the present invention is to provide a novel compound which can serve as a radical polymerization initiator, which has high absorbance to i-line (wavelength: 365 nm), which is resistant to bleeding out, which has high crystallinity, and which can be produced in a simple manner. Another object is to provide a production method therefor. Still another object is to provide a radical polymerization initiator. Yet another object is to provide a photocurable composition.

Means for Solving the Problems

The present inventors have conducted extensive studies in order to attain the aforementioned objects, and have found that a compound represented by the following formula (A) can be used as a radical polymerization initiator, has high absorbance to i-line, resistance to bleeding out, and high crystallinity, and can be readily produced. The present invention has been accomplished on the basis of this finding.

Accordingly, in a first mode of the present invention, there is provided 2,2-dimethoxy-1,2-di-[4-(meth)acryloyloxy]phenylethan-1-one represented by the following formula (A):

[F1]

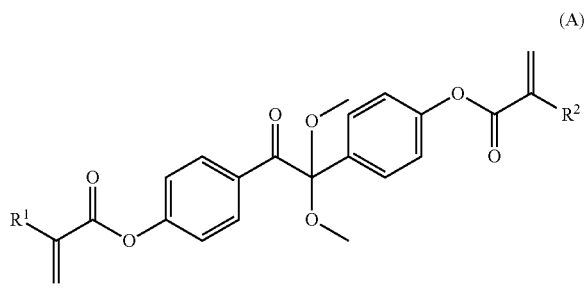

(A)

(wherein $R^1$ and $R^2$, which may be identical to or different from each other, each represent a hydrogen atom or a methyl group).

In a second mode, there is provide a radical polymerization initiator, characterized by being 2,2-dimethoxy-1,2-di-[4-(meth)acryloyloxy]phenylethan-1-one of the first mode.

In a third mode of the present invention, there is provided a photocurable composition, characterized by comprising 2,2-dimethoxy-1,2-di-[4-(meth)acryloyloxy]phenylethan-1-one of the first mode.

A fourth mode of the invention is directed to a specific embodiment of the photocurable composition of the third mode, which further contains a radical-polymerizable compound.

In a fifth mode of the present invention, there is provided a method for producing 2,2-dimethoxy-1,2-di-[4-(meth)acryloyloxy]phenylethan-1-one represented by the following formula (A):

[F2]

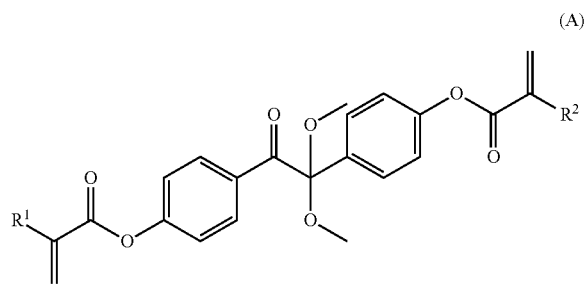

(A)

(wherein $R^1$ and $R^2$, which may be identical to or different from each other, each represent a hydrogen atom or a methyl group), characterized in that the method comprises reacting 4,4'-dihydroxybenzil with trimethyl orthocarboxylate in the presence of an acid catalyst, and then reacting the reaction mixture with a compound having a (meth)acryloyloxy group.

Effects of the Invention

According to the present invention, 2,2-dimethoxy-1,2-di-[4-(meth)acryloyloxy]phenylethan-1-one represented by the above formula (A), having a 2,2-dimethoxy-1,2-diphenylethane-1-one structure, can be used as a radical polymerization initiator. Since the compound has higher absorbance to i-line (wavelength: 365 nm), the compound can effectively utilize i-line, which is a predominant wavelength component of high-pressure mercury lamps and other industrially useful light sources. In addition, the (meth)acryloyloxy groups of the compound prevent bleeding out. Furthermore, by virtue of high crystallinity, the compound can be isolated at high purity through a simple crystallization process, without performing any particular purification process such as distillation or column chromatography.

MODES FOR CARRYING OUT THE INVENTION

Hereinafter, the present invention will be described in detail.

The novel compound of the present invention is a compound represented by the following formula (A):

[F3]

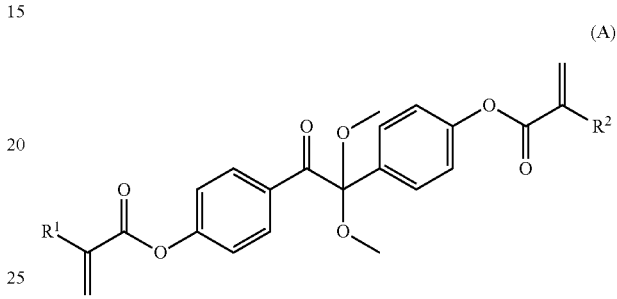

(A)

(wherein $R^1$ and $R^2$, which may be identical to or different from each other, each represent a hydrogen atom or a methyl group); i.e., 2,2-dimethoxy-1,2-di-[4-(meth)acryloyloxy]phenylethan-1-one.

As used herein, the term "(meth)acryloyl" collectively refers to acryloyl and methacryloyl. $R^1$ and $R^2$ may be identical to or different from each other. However, R' and $R^2$ are preferably identical to each other, since the homo-type compound can be easily synthesized.

As described above, since 2,2-dimethoxy-1,2-di-[4-(meth)acryloyloxy]phenylethan-1-one represented by the above formula (A) has a structure derived from 2,2-dialkyloxy-1,2-diphenylethan-1-one, the compound undergoes self-cleavage through irradiation with light such as a UV ray (e.g., light having a wavelength of 200 nm to 400 nm, preferably 313 nm to 365 nm), whereby radicals are effectively generated at low temperature (e.g., room temperature) within a short period of time. Thus, the compound represented by the above formula (A) can be used as a radical polymerization initiator. By virtue of a structure derived from 2,2-dialkyloxy-1,2-diphenylethan-1-one, the compound has higher absorbance to light having a wavelength of 365 nm and can effectively utilize i-line (wavelength: 365 nm), which is a predominant component of high-pressure mercury lamps and other industrially useful light sources.

The compound represented by the above formula (A) has (meth)acryloyloxy groups respectively bonded to the two phenyl groups. Thus, when the compound is used as a radical polymerization initiator of a photocurable composition, the (meth)acryloyloxy groups are also polymerized during polymerization of a radical-polymerizable compound (radical-polymerizable monomer), and the compound represented by the above formula (A) and cleavage fragments of the compound (A) are retained in the photocured product. Therefore, bleeding out of a component originating from the radical polymerization initiator, which would otherwise be caused with lapse of time after photocuring, can be considerably prevented. The photocurable composition may be formed from the compound represented by the above formula (A) and no additional radical-polymerizable compound other than compound (A). Also in this case, since the (meth)acryloyloxy groups of the compound represented by the above formula (A) undergo polymerization, thereby being retained in the photocured product, bleeding out can be prevented substantially.

Other than acetophenone-type radical generators; such as the compound represented by the above formula (A), which undergoes self-cleavage to generate radicals, a benzophenone-type radical generator is used. The benzophenone-type radical generator generates ketyl radicals via extraction of hydrogen from a hydrogen donor present in the vicinity of the radical generator through absorption of light such as a UV ray. Even in the case where the benzophenone-type radical generator has (meth)acryloyloxy groups, a hydrogen donor must be simultaneously added to the polymerization system. The hydrogen donor may serve as another bleeding out source, which is problematic. Also, since radical generation is attributed to intermolecular reaction with the hydrogen donor, radical generation requires a considerably period of time. Therefore, use of a benzophenone-type radical generator cannot attain the objects of the present invention.

In the compound represented by the above formula (A), a (meth)acryloyloxy group is directly bonded to a specific position (4-position) of a phenyl group of 2,2-dimethoxy-1,2-diphenylethan-1-one. Therefore, the compound (A) has high crystallinity. Accordingly, the compound (A) can be produced through crystallization, which enables easy production on an industrial scale, without performing a particular purification process such as distillation (possibly causing thermal decomposition or thermal polymerization) or column chromatography (high-cost). That is, high-purity crystals of the compound (A) can be readily produced.

As shown in the below-described Comparative Examples, a compound represented similar to that represented by the above formula (A) in which the methoxy group is changed to an ethoxy group has low crystallinity, and assumes the form of oil at production temperature; as do a compound similar to that represented by the above formula (A) in which each (meth)acryloyloxy group is bonded to the 2- or 3-position of a phenyl group; a compound similar to that represented by the above formula (A) in which each (meth)acryloyloxy group is not directly bonded to a phenyl group but bonded thereto via a spacer such as —CH$_2$COO— or —CH$_2$O—, and similar compounds. When the crystallinity is low, and the compound is oily at production temperature (e.g., about 0° C. to about 60° C.), a purification process such as distillation or column chromatography must be added, which is problematic.

No particular limitation is imposed on the method for producing the compound represented by the above formula (A). In one production procedure, 4,4'-dihydroxybenil is reacted with trimethyl orthocarboxylate in the presence of an acid catalyst, and the reaction product is further reacted with a compound having a (meth)acryloyloxy group.

Firstly, 4,4'-dihydroxybenzil and trimethyl orthocarboxylate are diluted with an organic solvent containing, for example, an alkyl alcohol, and the two compound are allowed to react in the presence of an acid catalyst, whereby 4,4'-dihydroxybenzil is acetalized.

4,4'-dihydroxybenzil may be produced from 4,4'-dimethoxybenzil, which is readily available on the market. Specifically, HBr is reacted with 4,4'-dimethoxybenzil.

Examples of the trimethyl orthocarboxylate include trimethyl orthoformate, trimethyl orthoacetate, trimethyl orthochloroacetate, trimethyl orthopropionate, trimethyl orthobutyrate, trimethyl orthoisobutyrate, trimethyl orthovalerate, and trimethyl orthobenzoate. Among the trimethyl orthocarboxylates, trimethyl orthoformate is particularly preferred, since it is most generally used at low cost.

Examples of the alkyl alcohol include C1 to C4 linear-chain or branched alkyl alcohols. Of these, methanol is preferred. In this case, the number of carbons of the alkyl group of the alkyl alcohol solvent (diluent) equals to that of each alkyl group of the trimethyl orthocarboxylate, and no by-product is generated from trans-acetalization (acetal exchange).

Examples of the acid catalyst include a Broensted acid and a Lewis acid. Examples Broensted acid include sulfuric acid, hydrogen chloride, trifluoroacetic acid, methanesulfonic acid, p-toluenesulfonic acid, and trifluoromethanesulfonic acid. Examples of the Lewis acid include those stable in aqueous solution; e.g., cerium(III) trifluoromethanesulfonate, hafnium(IV) trifluoromethanesulfonate, lanthanum(III) trifluoromethanesulfonate, yttrium(III) trifluoromethanesulfonate, neodymium(III) trifluoromethanesulfonate, and indium(III) trifluoromethanesulfonate. Needless to say, the acid catalyst is not limited to the above acid species.

No particular limitation is imposed on the reaction between 4,4'-dihydroxybenzil and trimethyl orthocarboxylate in the presence of an acid catalyst. In one case, the reaction is performed at 0 to 70° C. for 10 to 100 hours.

After completion of the reaction between 4,4'-dihydroxybenzil and trimethyl orthocarboxylate in the presence of an acid catalyst, a compound having a (meth)acryloyloxy group is caused to react with the reaction product, to thereby directly bond the (meth)acryloyloxy group to a specific position (4-position) of a phenyl group, whereby the compound represented by the above formula (A) can be produced.

Examples of the compound having a (meth)acryloyloxy group include (meth)acrylic acid, (meth)acryl halide, and (meth)acrylic anhydride.

No particular limitation is imposed on the conditions under which the compound having a (meth)acryloyloxy group is caused to react with the reaction product obtained by the reaction between 4,4'-dihydroxybenzil and trimethyl orthocarboxylate in the presence of an acid catalyst. In one case, the reaction is performed at 10 to 100° C. for 1 to 10 hours.

After the reaction with the compound having a (meth)acryloyloxy group, the compound represented by the above formula (A) can be isolated at high purity through a simple crystallization process such as recrystallization or crystallization, without performing a complex purification process such as distillation or column chromatography.

As described above, the compound represented by the above formula (A) serves as a radical polymerization initiator. In addition, the compound (A) has radical-polymerizable (meth)acryloyloxy groups, a photocurable composition can be produced from the compound represented by the above formula (A) and no additional radical-polymerizable compound other than compound (A). Such a photocurable composition may be used in various fields including UV-curable ink for lithography, flexography, and silk screening, solder resist, etching resist for production of industrial electronic material or the like, color filter resist, UV powder coating, aqueous UV coating, coating with UV-absorber, wood article finish coating, plastics, metal coating, etc. In one embodiment, the compound represented by the above formula (A) is diluted with a solvent (a non-polymerizable compound), to thereby provide the photocurable composition of the present invention. Alternatively, the compound represented by the above formula (A), as a single component, is irradiated with light, to thereby form a photocured product.

Examples of the diluent (solvent) include ketone compounds such as acetone, methylethyl ketone, and cyclohexanone; ester compounds such as methyl acetate, ethyl acetate, butyl acetate, ethyl lactate, and methoxyethyl acetate; ether compounds such as diethyl ether, ethylene glycol dimethyl ether, ethylcellosolve, butylcellosolve, phenylcellosolve, and dioxane; aromatic compounds such as toluene and xylene; aliphatic compounds such as pentane and hexane; halo-hydrocarbons such as methylene chloride, chlorobenzene, and chloroform; and alcohols such as methanol, ethanol, n-propanol, and isopropanol.

Needless to say, the photocurable composition of the present invention may further contain an additional radical-polymerizable compound in addition to the compound represented by the above formula (A).

The radical-polymerizable compound is a compound having one or more radical-polymerizable groups in the molecule thereof. Needless to say, the radical-polymerizable compound may have a radical-polymerizable group or groups of a single species or radical-polymerizable groups of two or more species. Also, one or more radical-polymerizable compounds may be used.

Examples of the radical-polymerizable compound having only one radical-polymerizable group in the molecule thereof include mono-functional (meth)acrylate monomers such as (meth)acrylic acid, methyl (meth)acrylate, ethyl (meth)acrylate, propyl (meth)acrylate, n-butyl (meth)acrylate, t-butyl (meth)acrylate, 2-ethylhexyl (meth)acrylate, n-nonyl (meth)acrylate, cyclohexyl (meth)acrylate, benzyl (meth)acrylate, dicyclopentenyl (meth)acrylate, 2-dicyclopentenoxyethyl (meth)acrylate, glycidyl (meth)acrylate, methoxyethyl (meth)acrylate, ethoxyethyl (meth)acrylate, butoxyethyl (meth)acrylate, methoxyethoxyethyl (meth)acrylate, ethoxyethoxyethyl (meth)acrylate, tetrahydrofurfuryl (meth)acrylate, 2-hydroxyethyl (meth)acrylate, 2-hydroxypropyl (meth)acrylate, 4-hydroxybutyl (meth)acrylate, cyclohexanedimethanol mono(meth)acrylate, 2-hydroxyethyl (meth)acrylate, hydroxypropyl (meth)acrylate, hydroxybutyl (meth)acrylate, phenyl (meth)acrylate, phenoxyethyl (meth)acrylate, phenoxyethoxyethyl (meth)acrylate, 2-hydroxy-3-phenoxypropyl (meth)acrylate, biphenyl (meth)acrylate, biphenoxyethyl (meth)acrylate, biphenoxyethoxyethyl (meth)acrylate, naphthalene (meth)acrylate, naphthaleneoxyethyl (meth)acrylate, naphthaleneoxyethoxyethyl (meth)acrylate, phenanthrene (meth)acrylate, phenanthreneoxyethyl (meth)acrylate, phenanthreneoxyethoxyethyl (meth)acrylate, anthracene (meth)acrylate, anthraceneoxyethyl (meth)acrylate, anthraceneoxyethoxyethyl (meth)acrylate, norbornyl (meth)acrylate, dicyclopentanyl (meth)acrylate, dicyclopentenyl (meth)acrylate, dicyclopentanyloxyethyl (meth)acrylate, dicyclopentenyloxyethyl (meth)acrylate, phenylepoxy (meth)acrylate, (meth)acryloylmorpholine, diacetone(meth)acrylamide, N-[2-(meth)acryloyiethyl]-1,2-cyclohexane dicarboimide, N-[2-(meth)acryloylethyl]-1,2-cyclohexane dicarboimid-1-ene, and N-[2-(meth)acryloylethyl]-1,2-cyclohexane dicarboimid-4-ene; and vinyl monomers such as N-vinylpyrrolidone, styrene, α-methylstyrene, vinyltoluene, 4-hydroxystyrene, allyl acetate, vinyl acetate, vinyl propionate, and vinyl benzoate.

Examples of the radical-polymerizable compound having two radical-polymerizable groups in the molecule thereof include bi-functional (meth)acrylate monomers such as diethylene glycol di(meth)acrylate, triethylene glycol di(meth)acrylate, polyethylene glycol di(meth)acrylate, 1,3-butylene glycol di(meth)acrylate, 1,4-butanediol di(meth)acrylate, tripropylene glycol di(meth)acrylate, polypropylene glycol di(meth)acrylate, 1,6-hexanediol di(meth)acrylate, 1,9-nonanediol di(meth)acrylate, neopentyl glycol di(meth)acrylate, neopentyl glycol pivalate di(meth)acrylate, bis(oxymethyl)tricyclo[5.2.1.0(2,6)]decane di(meth)acrylate, 2,2-bis(4-(acryloxydiethoxy)phenyl)propane, 2,2-bis(4-(methacryloxydiethoxy)phenyl)propane, tricyclo[5.2.1.0(2,6)]decane-3,8-diyl dimethyl dimethacrylate, bispehnol-A diglycydyl ether di(meth)acrylate, ethylene oxide-modified 1,4-cyclohexanedimethanol diacrylate, ethylene oxide-modified tetrabromobisphenol-A di(meth)acrylate, phenyl di(meth)acrylate, phenyldioxyethyl (meth)acrylate, phenyldioxyethoxyethyl (meth)acrylate, biphenyl di(meth)acrylate, hiphenyldioxyethyl (meth)acrylate, biphenyldioxyethoxyethyl (meth)acrylate, naphthalene di(meth)acrylate, naphthalenedioxyethyl (meth)acrylate, naphthalenedioxyethoxyethyl (meth)acrylate, phenanthrene di(meth)acrylate, phenanthrenedioxyethyl (meth)acrylate, phenanthrenedioxyethoxyethyl (meth)acrylate, anthracene di(meth)acrylate, anthracenedioxyethyl (meth)acrylate, and anthracenedioxyethoxyethyl (meth)acrylate.

Examples of the photo-polymerizable compound having three or more radical-polymerizable groups in the molecule thereof include 3- to 6-functional (meth)acrylate monomers such as phenyl tri(meth)acrylate, phenyltrioxyethyl (meth)acrylate, phenyltrioxyethoxyethyl (meth)acrylate, biphenyl tri(meth)acrylate, biphenyltrioxyethyl (meth)acrylate, biphenyltrioxyethoxyethyl (meth)acrylate, naphthalene tri(meth)acrylate, naphthalenetrioxyethyl (meth)acrylate, naphthalenetrioxyethoxyethyl (meth)acrylate, phenanthrene tri(meth)acrylate, phenanthrenetrioxyethyl (meth)acrylate, phenanthrenetrioxyethoxyethyl (meth)acrylate, anthracene tri(meth)acrylate, anthracenetrioxyethyl (meth)acrylate, anthracenetrioxyethoxyethyl (meth)acrylate, trimethylolpropane tri(meth)acrylate, trimethylolpropaneethoxy tri(meth)acrylate, tetramethylolmethane tri(meth)acrylate, tetramethylolmethane tetra(meth)acrylate, pentaerythritol tri(meth)acrylate, pentaerythritol tetra(meth)acrylate, ditrimethylolpropane tetra(meth)acrylate, dipentaerythritol hexa(meth)acrylate, and tris(2-hydroxyethyl)isocyanurate tri(meth)acrylate.

Examples of the oligomer-type radical-polymerizable compound having two or more radical-polymerizable groups in the molecule thereof include oligomer (meth)acrylates such as urethane (meth)acrylate and ester (meth)acrylate.

The photocurable composition of the present invention may further contain an additional radical polymerization initiator other than the compound represented by the above formula (A). Examples of the additional radical polymerization initiator include acetophenone, benzophenone, benzyl dialkyl ketal, α-hydroxyalkylphenones, α-aminoalkylphenones, acylphosphine oxides, titanocenes, oxime esters, trihalomethyltriazines, and other trihalomethyl-group-having compounds.

So long as the effects of the present invention are not impaired, the photocurable composition of the present invention may further contain an additive. Examples of the additive include a photo-sensitizer, a photo-non-curable oligomer, a photo-non-curable polymer, an adhesion promoter (e.g., a silane coupling agent), an organic solvent, a leveling agent, a plasticizer, a filler, a defoaming agent, a flame-retardant, a stabilizer, an anti-oxidant, a perfume, a thermal cross-linking agent, and a polymerization-inhibitor. These additives may be used singly or in combination of two or more species.

Examples of the organic solvent to be added to the photocurable composition include ketone compounds such as acetone, methylethyl ketone, and cyclohexanone; ester compounds such as methyl acetate, ethyl acetate, butyl acetate, ethyl lactate, and methoxyethyl acetate; ether compounds such as diethyl ether, ethylene glycol dimethyl ether, ethylcellosolve, butylcellosolve, phenylcellosolve, and dioxane; aromatic compounds such as toluene and xylene; aliphatic compounds such as pentane and hexane; halo-hydrocarbons such as methylene chloride, chlorobenzene, and chloroform; and alcohols such as methanol, ethanol, n-propanol, and isopropanol.

No particular limitation is imposed on the amount of the compound represented by the above formula (A) contained in the photocurable composition of the present invention. The amount of the compound represented by the above formula (A) is preferably, for example, 0.1 to 60 mass %, more preferably 0.5 to 30 mass %, most preferably 1 to 10 mass %.

When such a photocurable composition is irradiated with light having a wavelength of, for example, 200 to 400 nm, the compound represented by the above formula (A) undergoes self-cleavage, to thereby generate radicals. In the presence of the radicals serving as initiation species, the compound represented by the above formula (A) and an additional radical-polymerizable compound are polymerized, to thereby form a photocured product. Since the compound represented by the above formula (A) has two (meth)acryloyloxy groups bonded to respective phenyl groups, the compound represented by the above formula (A) and compounds formed by cleavage of the compound represented by the above formula (A) are retained in the photocured product. Thus, bleeding out of radical polymerization initiator components occurring with lapse of time after photocuring, which is a problem to be solved by the invention, can be considerably prevented.

EXAMPLES

The present invention will next be described in more detail by way of examples, which should not be construed as limiting the invention thereto. In the following Synthesis Examples, purity of each compound was determined through high-performance liquid chromatography (HPLC) under the following HPLC analysis conditions.
Column: SUPERIOREX ODS, product of SHISEIDO
Eluent: Mixture of acetonitrile and water 80:20 (by vol.)
Detection wavelength: 254 nm Synthesis Example 1

Synthesis of 4,4'-dihydroxybenzil

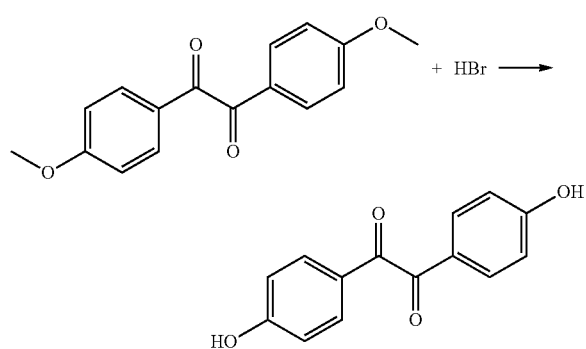

4,4'-Dimethoxybenzil (5.0 g) was dissolved in acetic acid (95 mL). To the solution, 48 mass % aqueous HBr (31.2 g) was added dropwise at 70° C. over 10 minutes. After addition of HBr, the mixture was stirred at 110° C. for 70 hours. Subsequently, water (150 g) was added to the mixture, to thereby crystallize the product. The crude crystals were recovered through filtration and washed with water (250 g), followed by drying, to thereby yield 4.0 g of 4,4'-dihydroxybenzil as a target product.

Synthesis Example 2

Synthesis of 2,2-dimethoxy-1,2-di-(4-methacryloyloxy)phenylethan-1-one

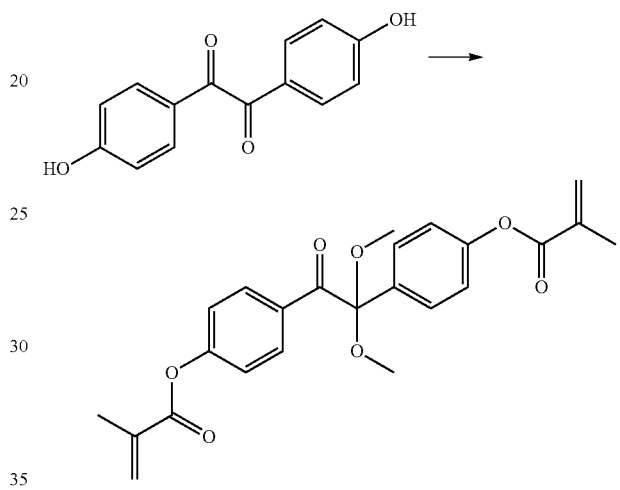

4,4'-Dihydroxybenzil (1.6 g) and sulfuric acid (0.16 g) were dissolved in methanol (12.8 g), and the solution was maintained at 25° C. To the solution, trimethyl orthoformate (4.2 g) was added dropwise, and the mixture was stirred for 15 hours. Then, triethylamine (3.0 g) was added at 30° C. to the mixture, and the resultant mixture was stirred for 5 minutes. The solvent methanol was distilled out. Acetonitrile (14 g) was added to the residue, to thereby crystallize the product. The crystals were recovered through filtration and dispersed in acetonitrile (14 g). To the dispersion, triethylamine (1.7 g) and dimethylaminopyridine (0.081 g) were added. Separately, methacrylic anhydride (2.5 g) was diluted with acetonitrile (5.0 g), and the liquid was added dropwise to the mixture at 30° C. After addition, the resultant mixture was stirred at 25° C. for 2 hours, and 3 mass % aqueous $NaHCO_3$ (64 g) was added, followed by stirring for 5 minutes. Then, the mixture was subjected to extraction with toluene (32 g), and the organic layer was washed thrice with water (each 10 g) and once with saturated brine (10 g). Subsequently, methoquione (2.50 mg) was added to the washed organic layer, and then the solvent was distilled out. Seed crystals (0.02 g) were added to the residue, and the solid was dried, to thereby yield 1.65 g of 2,2-dimethoxy-1,2-di-(4-methacryloyloxy)phenylethan-1-one as a white solid. The product was found to have a purity of 98.6% and a melting point of 85° C. The $^1$H-NMR data of the compound were as follows.

$^1$H-NMR ($CDCl_3$, ppm): δ=2.03 (s, 6H, methyl group), 3.23 (s, 6H, methyl group), 5.74 (s, 1H, vinyl group), 5.76 (s, 1H, vinyl group), 6.32 (s, 2H, vinyl group), 7.09 (d, 2H, benzene ring), 7.14 (d, 2H, benzene ring), 7.63 (d, 2H, benzene ring), 8.13 (d, 2H, benzene ring)

Synthesis Example 3

Synthesis of 2,2-dimethoxy-1,2-di-(4-acryloyloxy)phenylethan-1-one

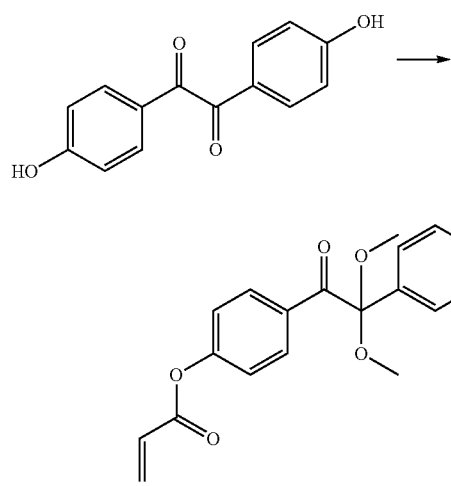

4,4-Dihydroxybenzil (1.6 g) and sulfuric acid (0.16 g) were dissolved in methanol (12.8 g), and the solution was maintained at 25° C. To the solution, trimethyl orthoformate (4.2 g) was added dropwise, and the mixture was stirred for 15 hours. Then, triethylamine (3.0 g) was added at 30° C. to the mixture, and the resultant mixture was stirred for 5 minutes. The solvent methanol was distilled out. Acetonitrile (14 g) was added to the residue, to thereby crystallize the product. The crystals were recovered through filtration and dispersed in acetonitrile (14 g). The dispersion was maintained at 15° C. To the dispersion, triethylamine (1.7 g) and dimethylaminopyridine (0.081 g) were added. Separately, acryl chloride (1.5 g) was diluted with acetonitrile (3.0 g), and the liquid was added dropwise to the mixture at 20° C. After addition, the resultant mixture was stirred at 15° C. for 1 hour, and 3 mass % aqueous $NaHCO_3$ (64 g) was added, followed by stirring for 5 minutes. Then, the mixture was subjected to extraction with toluene (32 g), and the organic layer was washed thrice with water (each 10 g) and once with saturated brine (10 g). Subsequently, methoquione (2.50 mg) was added to the washed organic layer, and then the solvent was distilled out. Hexane (4 g) was added to the residue, and the formed crystals were dried, to thereby yield 1.78 g of 2,2-dimethoxy-1,2-di-(4-acryloyloxy)phenylethan-1-one as a white solid. The product was found to have a purity of 99.6% and a melting point of 75° C. The $^1$H-NMR data of the compound were as follows.

$^1$H-NMR ($CDCl_3$, ppm): δ=3.22 (s, 6H, methyl group), 6.00 (d, 1H, vinyl group), 6.03 (d, 1H, vinyl group), 6.28 (d, 1H, vinyl group), 6.30 (d, 1H, vinyl group), 6.58 (d, 1H, vinyl group), 6.59 (d, 1H, vinyl group), 7.11 (d, 2H, benzene ring), 7.16 (d, 2H, benzene ring), 7.64 (d, 2H, benzene ring), 8.14 (d, 2H, benzene ring)

Comparative Synthesis Example 1

Synthesis of 2,2-diethoxy-1,2-di-(4-methacryloyloxy)phenylethan-1-one

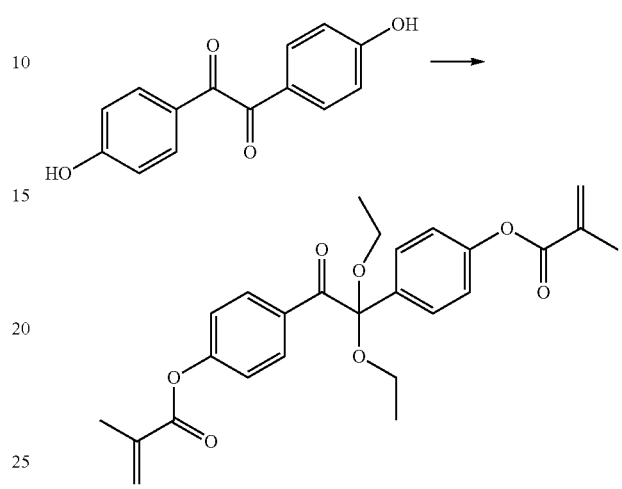

The procedure of Synthesis Example 2 was repeated, except that trimethyl orthoformate was changed to triethyl orthoformate, that sulfuric acid was changed to cerium(III) trifluoromethanesulfonate, and that purification was performed through column chromatography (ethyl acetate:hexane=1:5 (vol.)) after addition of methoquinone and removal of the solvent through distillation, to thereby produce 2,2-diethoxy-1,2-di-(4-methacryloyloxy)phenylethan-1-one as colorless oil at a yield of 56 mol % and a purity of 94.6%. The $^1$H-NMR data of the compound were as follows. $^1$H-NMR ($CDCl_3$, ppm): δ=1.21 (t, 6H, methyl group), 2.03 (s, 6H, methyl group), 3.43 (m, 4H, methylene group), 5.74 (s, 1H, vinyl group), 5.76 (s, 1H, vinyl group), 6.32 (s, 2H, vinyl group), 7.07 (d, 2H, benzene ring), 7.12 (d, 2H, benzene ring), 7.66 (d, 2H, benzene ring), 8.14 (d, 2H, benzene ring)

Comparative Synthesis Example 2

Synthesis of 3,3'-dimethoxybenzil

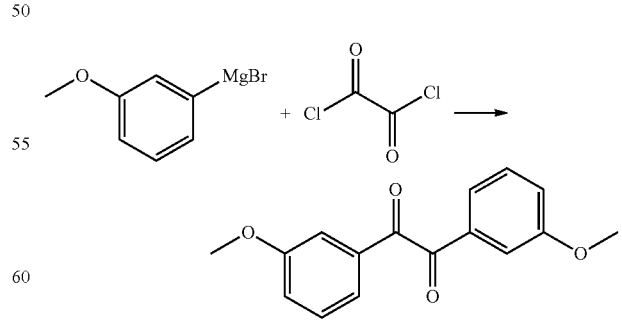

The synthesis method disclosed in Non-Patent Document 1 was carried out by use of 3-methoxybromobenzene as a staring material, to thereby produce 3,3'-dimethoxybenzil at a yield of 64 moil.

Comparative Synthesis Example 3

Synthesis of 3,3'-dihydroxybenzil

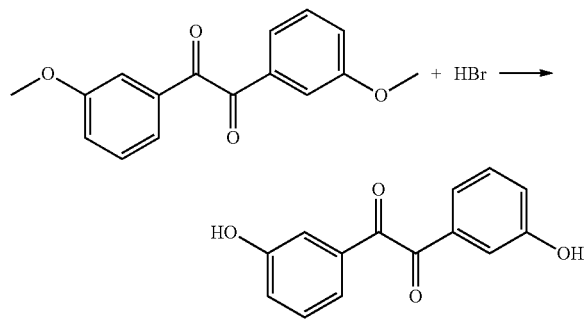

The procedure of Synthesis Example 1 was repeated, except that 3,3'-dimethoxybenzil was used as a stating material instead of 4,4'-dimethoxybenzil, to thereby produce target 3,3'-dihydroxybenzil at a yield of 90 mol %.

Comparative Synthesis Example 4

Synthesis of 2,2-dimethoxy-1,2-di-(3-methacryloyloxy)phenylethan-1-one

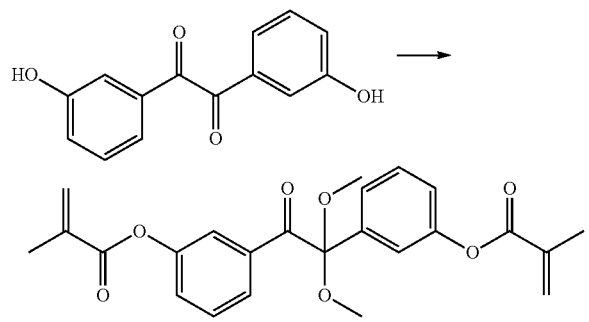

The procedure of Synthesis Example 2 was repeated, except that 4,4'-dihydroxybenzil was changed to 3,3'-dihydroxybenzil, that stirring was performed for 48 hours after addition of trimethyl orthoformate, and that purification was performed through column chromatography (ethyl acetate: hexane=1:9) after addition of methoquinone and removal of the solvent through distillation, to thereby produce 2,2-dimethoxy-1,2-di-(3-methacryloyloxy)phenylethan-1-one as colorless oil at a yield of 48 mol % and a purity of 98.2%. The $^1$H-NMR data of the compound were as follows.

$^1$H-NMR (CDCl$_3$, ppm): δ=2.05 (s, 6H, methyl group), 3.24 (s, 6H, methyl group), 5.76 (s, 2H, vinyl group), 6.34 (s, 2H, vinyl group), 7.11 (d, 1H, benzene ring), 7.24 (d, 1H, benzene ring), 7.36 (m, 3H, benzene ring), 7.48 (s, 1H, benzene ring), 7.83 (s, 181, benzene ring), 7.94 (d, 1H, benzene ring)

Comparative Synthesis Example 5

Synthesis of 2,2-dimethoxy-1,2-di-[4-(2-chloro)-acetoxy]-phenylethan-1-one

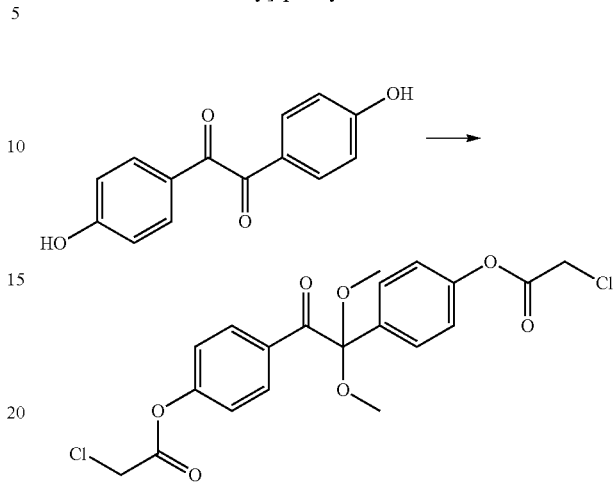

The procedure of Synthesis Example 3 was repeated, except that acryl chloride was changed to chloroacetyl chloride, and that no operation was performed after addition of methoquinone and removal of the solvent through distillation, to thereby produce target 2,2-dimethoxy-1,2-di-[(4-(2-chloro)acetoxy]-phenylethan-1-one as a crude product at a yield of 58 mol %.

Comparative Synthesis Example 6

Synthesis of 2,2-dimethoxy-1,2-di-[4-(2-methacryloyloxy)-acetoxy]-phenylethan-1-one

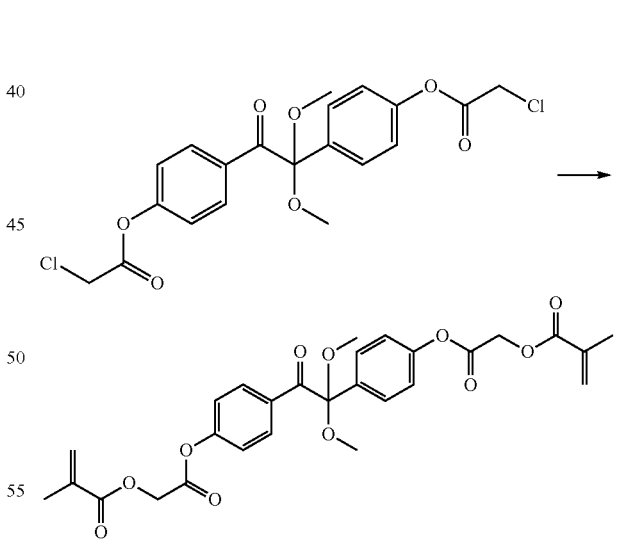

The crude 2,2-diethoxy-1,2-di-(4-(2-chloro)acetoxy)phenylethan-1-one (1.0 g) obtained in Comparative Synthesis Example 5 and sodium iodide (0.03 g) were dissolved in N,N-dimethylformamide (7.0 g). Potassium methacrylate (0.70 g) was added to the solution, and the mixture was stirred at 50° C. for 15 hours. Thereafter, 3 mass % aqueous NaHCO$_3$ was added to the mixture, and the resultant mixture was stirred for 5 minutes. Then, the mixture was subjected to extraction with toluene (20 g), and the organic layer was washed thrice with water (each 10 g) and once with saturated brine (10 g). Subsequently, methoquione (2.50 mg) was added to the washed organic layer, and then the solvent was distilled out. The residue was purified through column chromatography (ethyl acetate:hexane=1:1 (vol.)), to thereby produce 2,2-dimethoxy-1,2-di-[4-(2-methacryloyloxy)-acetoxy]-phenylethan-1-one as colorless oil at a yield of 58 mol % and a purity of 93.3%. The $^1$H-NMR data of the compound were as follows.

$^1$H-NMR (CDCl$_3$, ppm): δ=1.99 (s, 6H, methyl group), 3.21 (s, 6H, methyl group), 4.89 (s, 4H, methylene group), 5.68 (s, 2H, vinyl group), 6.24 (s, 2H, vinyl group), 7.09 (d, 2H, benzene ring), 7.14 (d, 2H, benzene ring), 7.62 (d, 2H, benzene ring), 8.11 (d, 2H, benzene ring)

Example 1

Benzyl acrylate (product name: V#160, product of Osaka Organic Chemical Industry Ltd.) (60 parts by mass), trimethylolpropane triacrylate (product name: Light Acrylate TMP-A, product of Kyoeisha Chemical Co., Ltd.) (36 parts by mass), and 2,2-dimethoxy-1,2-di-(4-methacryloyloxy) phenylethan-1-one (4 parts by mass) produced in Synthesis Example 2 were mixed with stirring at room temperature (25° C.), to thereby prepare a photocurable composition of Example 1.

Subsequently, the thus-prepared photocurable composition was applied on a glass substrate, and another glass substrate was stacked on the coated glass plate, to thereby fabricate a pair of glass plates sandwiching the photocurable composition. In this state, the photocurable composition was irradiated under nitrogen with light from a mercury-xenon lamp at 1 J/cm$^2$, to thereby cure the photocurable composition. After completion of curing, the cured product was peeled from the glass plates.

Next, the thus-obtained cured product was immersed in acetone for 15 hours, and the immersion liquid was analyzed through high-performance liquid chromatography (HPLC), whereby the amount of eluted 2,2-dimethoxy-1,2-di-(4-methacryloyloxy)phenylethan-1-one serving as a radical polymerization initiator from the cured product was determined. Table 1 shows the results.

Example 2

The procedure of Example 1 was repeated, except that 2,2-dimethoxy-1,2-di-(4-acryloyloxy)phenylethan-1-one (Synthesis Example 3) was used instead of 2,2-dimethoxy-1,2-di-(4-methacryloyloxy)phenylethan-1-one (Synthesis Example 2).

Comparative Example 1

The procedure of Example 1 was repeated, except that 2,2-dimethoxy-1,2-diphenylethan-1-one (product name: IRGACURE 651, product of BASF) was used instead of 2,2-dimethoxy-1,2-di-(4-methacryloyloxy)phenylethan-1-one (Synthesis Example 2).

Comparative Example 2

The procedure of Example 1 was repeated, except that 2-hydroxy-1-{4-[4-(2-hydroxy-2-methyl-propionyl)-benzyl]-phenyl}-2-methyl-propan-1-one (product name: IRGACURE 127, product of BASF) was used instead of 2,2-dimethoxy-1,2-di-(4-methacryloyloxy)phenylethan-1-one (Synthesis Example 2).

Comparative Example 3

The procedure of Example 1 was repeated, except that 1-[4-(2-hydroxyethoxy)-phenyl]-2-hydroxy-2-methyl-1-propan-1-one (product name: IRGACURE 2959, product of BASF) was used instead of 2,2-dimethoxy-1,2-di-(4-methacryloyloxy)phenylethan-1-one (Synthesis Example 2).

TABLE 1

|  | Ex. 1 | Ex. 2 | Comp. EX. 1 | Comp. EX. 1 | Comp. EX. 1 |
|---|---|---|---|---|---|
| Percent extraction of radical polymerization initiator (mass %) | <0.01 | <0.01 | 3.44 | 3.14 | 2.77 |

The compounds represented by the above formula (A) produced in Synthesis Examples 2 and 3 had solid form with very high crystallinity. In contrast, as compared with the compounds of Synthesis Examples 2 and 3, the compounds produced in Comparative Synthesis Examples 1 to 6 were oily with very low crystallinity. Furthermore, in Synthesis Examples 2 and 3, high-purity compounds were isolated only through crystallization, whereas a cumbersome purification process such as column chromatography was required in Comparative Synthesis Examples. As is clear from Table 1, in Examples 1 and 2, employing the compound represented by the above formula (A) as a radical polymerization initiator, bleeding out was substantially prevented.

The invention claimed is:

1. 2,2-Dimethoxy-1,2-di-[4-(meth)acryloyloxy]phenylethan-1-one represented by the following formula (A):

[F1]

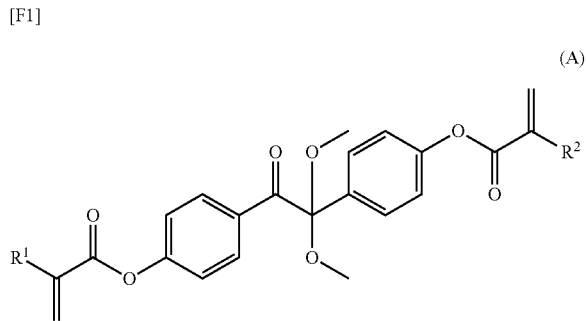

(A)

(wherein R$^1$ and R$^2$, which may be identical to or different from each other, each represent a hydrogen atom or a methyl group).

2. A radical polymerization initiator, characterized by being 2,2-dimethoxy-1,2-di-[4-(meth)acryloyloxy]phenylethan-1-one as recited in claim 1.

3. A photocurable composition, characterized by comprising 2,2-dimethoxy-1,2-di-[4-(meth)acryloyloxy]phenylethan-1-one as recited in claim 1.

4. A photocurable composition according to claim 3, which further contains a radical-polymerizable compound.

5. A method for producing 2,2-dimethoxy-1,2-di-[4-(meth)acryloyloxy]phenylethan-1-one represented by the following formula (A):

[F2]

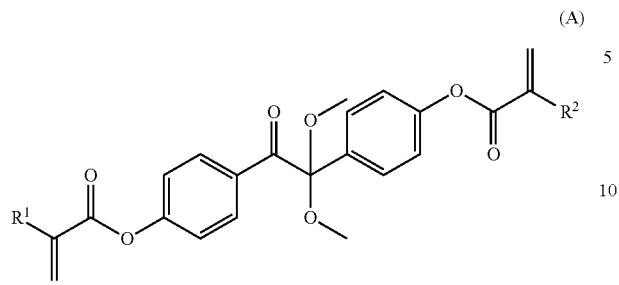

(wherein $R^1$ and $R^2$, which may be identical to or different from each other, each represent a hydrogen atom or a methyl group), characterized in that the method comprises reacting 4,4'-dihydroxybenzil with trimethyl orthocarboxylate in the presence of an acid catalyst, and then reacting the reaction mixture with a compound having a (meth)acryloyloxy group.

\* \* \* \* \*